(12) United States Patent
Fassberg et al.

(10) Patent No.: US 6,503,482 B1
(45) Date of Patent: Jan. 7, 2003

(54) NON-CHLOROFLUOROCARBON AEROSOL FORMULATIONS

(75) Inventors: Julianne Fassberg, New York, NY (US); Joel A. Sequeira, New York, NY (US); Imtiaz A. Chaudry, North Caldwell, NJ (US); Michael Kopcha, East Brunswick, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 08/157,188

(22) PCT Filed: Jun. 8, 1992

(86) PCT No.: PCT/US92/04618

§ 371 (c)(1),
(2), (4) Date: Dec. 9, 1993

(87) PCT Pub. No.: WO92/22287

PCT Pub. Date: Dec. 23, 1992

(51) Int. Cl.$^7$ .................................................. A61K 9/12
(52) U.S. Cl. .......................................... 424/46; 424/45
(58) Field of Search ....................... 424/45, 46; 514/958

(56) References Cited

U.S. PATENT DOCUMENTS

| | | | |
|---|---|---|---|
| 2,868,691 A | 1/1959 | Porush et al. | |
| 2,885,427 A | 5/1959 | Ruh et al. ................. | 260/653.7 |
| 3,261,748 A | 7/1966 | Larsen ......................... | 167/52 |
| 3,320,125 A | 5/1967 | Grim | |
| 3,644,353 A | 2/1972 | Lunts et al. .......... | 260/247.5 R |
| 4,129,603 A | 12/1978 | Bell ............................. | 260/653 |
| 4,174,295 A | 11/1979 | Bargigia et al. ............. | 252/305 |
| 4,311,863 A | 1/1982 | Gumprecht .................. | 570/170 |
| 4,851,595 A | 7/1989 | Gumprecht .................. | 570/170 |
| 4,967,024 A | 10/1990 | Gumprecht et al. ......... | 570/168 |
| 5,202,110 A * | 4/1993 | Dalby et al. .................. | 424/45 |
| 5,225,183 A * | 7/1993 | Purewal et al. ............... | 424/45 |
| 5,474,759 A * | 12/1995 | Fassberg et al. | |
| 5,674,471 A * | 10/1997 | Akehurst et al. | |
| 5,676,929 A | 10/1997 | Akehurst et al. | |
| 5,695,743 A * | 12/1997 | Purewal et al. | |
| 5,736,124 A | 4/1998 | Akehurst et al. | |

FOREIGN PATENT DOCUMENTS

| | | |
|---|---|---|
| EP | 0372777 | 6/1990 |
| EP | 0 379 793 | 8/1990 |
| EP | 0379793 | 8/1990 |
| EP | 0384371 | 8/1990 |
| EP | 0403301 | 12/1990 |
| GB | 9126378.0 | 12/1991 |
| GB | 9126405.1 | 12/1991 |
| GB | 9202522.0 | 2/1992 |
| WO | 9007333 | 7/1990 |
| WO | 9011754 | 10/1990 |
| WO | 9104011 | 4/1991 |
| WO | 9111173 | 8/1991 |
| WO | 9111495 | 8/1991 |
| WO | 9114422 | 10/1991 |
| WO | 9200061 | 1/1992 |
| WO | 9200062 | 1/1992 |
| WO | 9200107 | 1/1992 |
| WO | 9208446 | 5/1992 |
| WO | 92/11190 | 7/1992 |
| WO | 93/11743 | 6/1993 |
| WO | 93/11744 | 6/1993 |
| WO | 93/11747 | 6/1993 |

OTHER PUBLICATIONS

Budavari Et Al. (1989). The Merck Index, Merck & Co., Inc., Rahway, NJ pp. 158 and 982.*
Research Disclosure 16265, Oct. 1977.
Research Disclosure 30161, May 1989.
U.S. patent application Ser. No. 07/632,133, Marecki, filed Dec. 21, 1990.
U.S. patent application Ser. No. 07/878,039, Schultz et al., filed May 4, 1992.
U.S. Senate Hearings, May 12–14, 1987, pp. 347 and 437.

* cited by examiner

*Primary Examiner*—Jose' G. Dees
(74) *Attorney, Agent, or Firm*—Edward H. Mazer; Robert A. Franks

(57) ABSTRACT

Aerosol formulations substantially free of chlorofluorocarbons, for oral and/or nasal administration, are described. The formulations comprise 1,1,1,2-tetrafluoroethane, a medicament, optionally an excipient and optionally a surfactant. Methods of treatment using the formulations also are described.

9 Claims, No Drawings

NON-CHLOROFLUOROCARBON AEROSOL FORMULATIONS

INTRODUCTION TO THE INVENTION

The present invention is directed at aerosol formulations which are substantially free of chlorofluorocarbons (CFC's). More specifically, the present invention is directed at formulations substantially free of CFC's and having particular utility in medicinal applications, especially in metered dose pressurized inhalators (MDI's).

Metered dose inhalators have proven to be an effective method for delivering medicaments orally and nasally. They have been used extensively for delivering bronchodilating and steroidal compounds to asthmatics and may also be useful for delivering other compounds such as pentamidine and non-bronchodilator anti-inflammatory drugs. The rapid onset of activity of compounds administered in this manner and the absence of any significant side effects have resulted in a large number of compounds being formulated for administration via this route. Typically, the drug Is delivered to the patient by a propellant system generally comprising one or more propellants which have the appropriate vapor pressure and which are suitable for oral or nasal administration. The more preferred propellant systems typically comprise propellant 11, propellant 12, propellant 114 or mixtures thereof. Often the vapor pressure of the propellant systems is adjusted by admixing a liquid excipient with the propellant.

However, propellants 11, 12 and 114 belong to a class of compounds known as chlorofluorocarbons, which have been linked to the depletion of ozone in the atmosphere. It has been postulated that ozone blocks certain harmful UV rays and that a decrease in the atmospheric ozone content will result in an increase in the incidence of skin cancer. In the 1970's certain steps were taken to reduce the CFC emissions from aerosols. Other propellants, such as hydrocarbons, were used, or the product was delivered in a different manner. Because CFC usage in medicinal applications is relatively low i.e. less than 1% of total CFC emissions, and because of the health benefits associated with metered dose inhalators, steps were not taken at that time to restrict the use of CFC propellants in metered dose inhalators.

However, continuing and more sophisticated ozone measurements have indicated that the earlier restrictions in CFC usage were insufficient and that additional, significant steps should be taken to drastically reduce CFC emissions. Recently, recommendations have been made that CFC production be virtually discontinued by the end of this century. As a result, it may not be possible to continue to use CFC propellants in the intermediate and long term. While some efforts have been made to use non-pressurized metered dose inhalators, many of these devices have not been completely successful. Many do not deliver uniform doses, are mechanically complex, do not provide the 100–200 doses per unit of current aerosol containers, are difficult for individuals to utilize, are bulky and/or cumbersome for the patients to use, particularly when they have an acute need for the medication.

As a result, there is a need for aerosol formulations substantially free of CFC's. Non-CFC propellants must meet several criteria for pressurized metered dose inhalators. They must be non-toxic, stable and non-reactive with the medicament and the other major components in the valve/actuator. One propellant which has been found to be suitable is $CF_3$—$CH_2F$, also known as Freon 134a, HFA 134a, HFC 134a or 1,1,1,2 tetrafluoroethane. However, the physical properties, i.e. vapor pressure, polarity, solubility, density and viscosity of HFC 134a differ from those of commonly used propellants. Propellant HFC 134a has a vapor pressure of $5.84 \times 10^5$ newton/meter$^2$ absolute (84.7 psia), which is too high for use in metered dose inhalators. In addition, commonly used surfactants may be insoluble in HFC 134a. Moreover, where the medicament is to be delivered as a solution, the medicament may not be readily soluble in this propellant. The density and polarity difference between HFC 134a and the previously used CFC propellant may result in a different delivery of the medicament when HFC 134a replaces a CFC propellant. The medicament may cream, settle or agglomerate in the non-CFC propellant even though this did not occur in the CFC propellant.

The use of HFA 134a previously has been disclosed for use in medicinal inhalators. European Patent Publication No. 0 372 777 is directed at medicinal aerosol formulations incorporating Freon 134a and an adjuvant having a higher polarity than the propellant. This publication lists several possible adjuvants and surfactants for use in combination with the propellant and the medicament.

International patent application No. WO 91/04011 discloses the combination of 1,1,1,2 tetrafluoroethane and a powdered medicament pre-coated with a non-perfluorinated surfactant prior to dispersing the powdered medicament in the propellant. Pages 6–7 of the publication list suitable surfactants for use with the propellant. A perfluorinated adjuvant optionally could be added. However, the pre-coating of the medicament may not be advantageous, since it adds an additional, complex step to the manufacturing process.

*Research Disclosure* No. 30161, May 1989 discloses that non-CFC propellants such as fluorohydrocarbons may be used in pressurized medicaments delivered directly to the lungs e.g. bronchodilators.

U.S. Pat. No. 4,174,295 discloses the combination of HFC 134a with various chlorofluorocarbons and optionally a saturated hydrocarbon.

U.S. Pat. No. 2,885,427 discloses the use of HFC-134a as an aerosol propellant.

U.S. Pat. No. 3,261,748 discloses the use of HFC-134a for anesthesia.

U.S. Pat. Nos. 4,129,603, 4,311,863, 4.851,595 and European Publication No. 379,793 also disclose the use of HFC-134a as an aerosol propellant.

However, the specific combinations noted above may not provide the desired solubility, stability, low toxicity, exact dosage, correct particle size (if suspension) and/or compatibility with commonly used valves assemblies of metered dose inhalers.

SUMMARY OF THE INVENTION

The present invention is directed at non-toxic formulations substantially free of CFC's, having improved stability and compatibility with the medicament and valve components and which are relatively easily manufactured.

The present invention also is directed at formulations which may be utilized in present aerosol filling equipment with only relatively minor modifications and without pre-coating the medicament.

The invention includes an aerosol formulation comprising:

A. an effective amount of medicament; and

B. 1,1,1,2 tetrafluoroethane.

The formulation optionally may further comprise an excipient preferably selected from the group consisting of:
propylene glycol diesters of medium chain fatty acids;
triglyceride esters of medium chain fatty acids;
perfluorodimethylcyclobutane;
perfluorocyclobutane;
polyethylene glycol;
menthol;
lauroglycol;
diethylene glycol monoethylether;
polyglycolized glycerides of medium chain fatty acids;
alcohols;
eucalyptus oil;
short chain fatty acids;
and combinations thereof.

The formulation optionally may further comprise a surfactant. The surfactant preferably is selected from the group consisting of:
oleic acid;
sorbitan trioleate;
cetyl pyridinium chloride;
soya lecithin;
polyoxyethylene(20) sorbitan monolaurate;
polyoxyethylene(20) sorbitan monostearate;
polyoxyethylene(20) sorbitan monooleate;
polyoxypropylene-polyoxyethylene block copolymers;
polyoxyethylene (10) stearyl ether;
polyoxyethylene (2) oleyl ether;
polyoxypropylene-polyoxyethylene-ethylenediamine block copolymers;
castor oil ethoxylate; and combinations thereof.

The preferred liquid excipients are diethylene glycol monethyether, propylene glycol diesters of medium chain fatty acids, perfluorodimethylcyclobutane and polyethylene glycol.

The preferred surfactants are oleic acid; sorbitan trioleate, cetylpyridinium chloride; polyoxyethylene (20) sorbitan monolaurate; polyoxypropylene-polyoxyethylene block copolymers; soya lecthin; and polyoxypropylene-polyoxyethylene-ethylenediamine block copolymers; with oleic acid being particularly preferred.

The invention is of particular utility where the medicament is albuterol, mometasone furoate or beclomethasone dipropionate, and salts and clathrates thereof.

A formulation range comprises:

| A. | 1,1,1,2 tetrifluoroethane | 25–99.99 wt % |
|---|---|---|
| B. | medicament | 0.01–1 wt % |
| C. | excipient | 0–75 wt % |
| D. | surfactant (if present) | 0–3 wt % |

The present invention also is directed at a method of treating asthma in mammals comprising administering to a mammal in need of such treatment an effective amount of aerosol formulation comprising:
A. a medicament selected from the group comprising albuterol, mometasone furoate, beclomethasone dipropionate, and salts and clathrates thereof;
B. 1,1,1,2 tetrafluoroethane; and
C. optionally an excipient, preferably selected from the group consisting of:
propylene glycol diesters of medium chain fatty acids;
triglyceride esters of medium chain fatty acids;
perfluorodimethylcyclobutane;
perfluorocyclobutane;
polyethylene glycol;
menthol;
lauroglycol;
diethylene glycol monoethylether;
polyglycolized glycerides of medium chain fatty acids;
alcohols;
short chain fatty acids;
eucalyptus oil; and combinations thereof.

A surfactant optionally is present. The surfactant preferably is selected from the group consisting of:
oleic acid;
sorbitan trioleate;
cetyl pyridinium chloride;
soya lecithin;
polyoxyethylene (20) sorbitan monolaurate;
polyoxyethylene (20) sorbitan monostearate;
polyoxypropylene-polyoxyethylene block copolymers;
polyoxyethylene (10) stearyl ether
polyoxyethylene (2) oleyl ether
polyoxyethylene-polyoxypropylene-ethylene diamine block copolymers
castor oil ethoxylate; and combinations thereof.

DETAILED DESCRIPTION OF THE INVENTION

The formulations of the present invention all utilize propellant 134a in combination with the medicament, optionally a liquid excipient and optionally a surfactant. The excipient facilitates the compatibility of the medicament with the propellant and also lowers the discharge pressure to an acceptable range i.e. about $2.76–5.52 \times 10^5$ newton/meter$^2$ absolute (40 to 80 psia), preferably $3.45–4.83 \times 10^5$ newton/meter$^2$ absolute (50 to 70 psia). The excipient chosen must be non-reactive with the medicament, relatively non-toxic, and should have a vapor pressure below about $3.45 \times 10^5$ newton/meter$^2$ absolute (50 psia). As used hereinafter the term "medium chain fatty acids" refers to chains of alkyl groups terminating in a —COOH group and having 6–12 carbon atoms, preferably 8–10 carbon atoms. The term "short chain fatty acids" refers to chains of alkyl groups terminating in a —COOH group group and having 4–8 carbon atoms. The term "alcohol" includes $C_1–C_3$ alcohols, such as methanol, ethanol and isopropanol. Among the preferred excipients are:
propylene glycol diesters of medium chain fatty acids available under the tradename Miglyol 840 (from Hüls America, Inc. Piscataway, N.J.);
triglyceride esters of medium chain fatty acids available under the tradename Miglyol 812 (from Hüls);
perfluorodimethylcyclobutane available under the tradename Vertrel 245 (from E.I DuPont de Nemours and Co. Inc. Wilmington, Del.);
perflurocyclobutane available under the tradename octafluoro cyclobutane (from PCR Gainsville, Fla.);
polyethylene glycol available under the tradename PEG 400 (from BASF Parsippany, N.J.);
menthol (from Pluess-Stauffer International Stanford, Conn.);
propylene glycol monolaurate available under the tradename lauroglycol (from Gattefossé Elmsford, N.Y.);

diethylene glycol monoethylether available under the tradename Transcutol (from Gattefossé);

polyglycolized glyceride of medium chain fatty acids available under the tradename Labrafac Hydro WL 1219 (from Gattefossé);

alcohols, such as ethanol, methanol and isopropanol;

eucalyptus oil (available from Pluess-Stauffer International); and mixtures thereof.

A surfactant optionally may be added to lower the surface and interfacial tension between the medicament and the propellant. Where the medicament, propellant and excipient are to form a suspension, a surfactant may or may not be required. Where the medicament, propellant and excipient are to form a solution, a surfactant may or may not be necessary, depending in part on the solubility of the particular medicament and excipient. The surfactant may be any suitable, non-toxic compound which is non-reactive with the medicament and which substantially reduces the surface tension between the medicament, the excipient and the propellant and/or acts as a valve lubricant. Among the preferred surfactants are:

oleic acid available under the tradename oleic acid NF6321 (from Henkel Corp. Emery Group, Cincinnati, Ohio);

cetylpyridinium chloride (from Arrow Chemical, Inc. Westwood, N.J.);

soya lecithin available under the tradename Epikuron 200 (from Lucas Meyer Decatur, Ill.);

polyoxyethylene (10) stearyl ether available under the tradename Briji 76 (from ICI);

polyoxyethylene (2) oleyl ether available under the tradename Brij 92 (from ICI);

polyoxyethylene-polypropylene-ethylenediamine block copolymer available under the tradename Tetronic 150 R1 (from BASF);

polyoxyethylene(20) sorbitan monolaurate available under the tradename Tween 20 (from ICI Specialty Chemicals, Wilmington, Del.);

polyoxyethylene(20) sorbitan monostearate available under the tradename Tween 60 (from ICI);

polyoxyethylene(20) sorbitan monooleate available under the tradename Tween 80 (from ICI);

polyoxypropylene-polyoxyethylene block copolymers available under the tradenames Pluronic L-92, Pluronic L-121 and Pluronic F 68 (from BASF);

castor oil ethoxylate available under the tradename Alkasurf CO-40 (from Rhone-Poulenc Mississauga Ontario, Canada); and mixtures thereof.

The medicaments of the present invention may include any pharmaceutically active compounds which are to be delivered by oral inhalation or nasally. Typical classes of compounds include bronchodilators, anti-inflammatory compounds, antihistamines, antiallergics, analgesics, antitussives, anti-anginal medications, steroids, corticosteroids, vasoconstrictors and antibiotics. Specific compounds within these classes of compounds are albuterol, mometasone furoate, beclomethasone dipropionate, isoproterenol, heparin, terbutaline, rimiterol, perbuterol, disodium cromoglycate, isoprenaline, adrenaline, pentamidine and ipratropium bromide. These compounds may be utilized either as the free base, as a salt, or as a clathrate depending upon the stablity and solubility of the active compound in the specific formulation. Where clathrates are utilized, P-11 and hexane clathrates are particularly preferred.

Where the active compound forms a suspension, the particle size should be relatively uniform, with substantially all the particles preferably ranging between about 0.1–25 microns, preferably 0.5–10 microns, more preferably 1–5 microns. Particles larger than 25 microns may be held up in the oropharyngeal cavity, while particles smaller than about 0.5 micron preferably are not utilized, since they would be more likely to be exhaled and, therefore, not reach the lungs of the patient.

The formulations of the present invention may be filled into the aerosol containers using conventional filling equipment. Since propellant 134a may not be compatible with all elastomeric compounds currently utilized in present aerosol valve assemblies, it may be necessary to substitute other materials, such as white buna rubber, or to utilize excipients and optionally surfactants which mitigate the adverse effects of propellant 134a on the valve components. One may optionally use an actuator device with a spacer to reduce force of the spray from an MDI.

To assure uniform dispersion of the active ingredient, the formulations typically will include the following components:

|  | Range (wt %) | Preferred Range (wt %) | Most Preferred Range (wt %) |
| --- | --- | --- | --- |
| Medicament | 0.01–1 | 0.03–0.7 | 0.05–0.5 |
| Propellant | 25–99.99 | 50–99.97 | 50–99.95 |
| Excipient(s) | 0–75 | 0–50 | 0–50 |
| Surfactant(s) | 0–3 | 0–2 | 0–1 |

Depending on the particular application, the container may be charged with a predetermined quantity of formulation for single or multiple dosing. Typically, the container is sized for multiple-dosing, and, therefore, it is very important that the formulation delivered is substantially uniform for each dosing. For example, where the formulation is for bronchodilation, the container typically is charged with a sufficient quantity of the formulation for 200 charges.

Suitable suspensions may be screened in part by observing several physical properties of the formulation, i.e. the rate of particle agglomeration, the size of the agglomerates and the rate of particulate creaming/settling and comparing these to an acceptable standard. Suitable solutions may be screened by observing the solubility of the medicament over the entire recommended storage temperature range.

Suspensions of the present invention preferably may be prepared by either the pressure filling or cold filling procedures well-known in the art.

For metered dose inhalators, suspensions may be particularly preferred for efficacy and stability considerations.

Those skilled in the art may choose to add one or more preservative, buffer, antioxidant, sweetener and/or flavors or other taste masking agents depending upon the characteristics of the formulation.

Examples I–XXXII below further describe representative formulations of the present invention, some examples showing alternative formulations "A" and "B".

EXAMPLE I

| Component | wt % |
|---|---|
| Albuterol | 0.1 |
| Vetrel 245 | 9.9 |
| HFC-134a | 90.0 |

EXAMPLE II

| Component | wt % |
|---|---|
| Albuterol | 0.5 |
| Vetrel 245 | 49.9 |
| HFC-134a | 49.6 |

EXAMPLE III

| Component | wt % |
|---|---|
| Albuterol | 0.1 |
| Oleic Acid | 0.01 |
| Miglyol 840 | 9.0 |
| HFC 134a | 90.89 |

EXAMPLE IV

| Component | wt % |
|---|---|
| Albuterol | 0.1 |
| Tetronic 150 R1 | 0.1 |
| Miglyol 840 | 9.8 |
| HFC 134a | 90.0 |

EXAMPLE V

| Component | wt % |
|---|---|
| Albuterol | 0.1 |
| Pluronic L-121 | 0.1 |
| Miglyol 840 | 9.8 |
| HFC 134a | 90.0 |

EXAMPLE VI

| Component | wt % |
|---|---|
| Albuterol | 0.1 |
| Oleic acid | 0.2 |
| Transcutol | 18.0 |
| HFC 134a | 81.7 |

EXAMPLE VII

| Component | A wt % | B wt % |
|---|---|---|
| Albuterol | 0.10 | 0.10 |
| Oleic acid | 0.01 | 0.01 |
| Ethanol | 30.00 | 15.00 |
| HFC 134a | 69.89 | 84.89 |

EXAMPLE VIII

| Component | A wt % | B wt % |
|---|---|---|
| Albuterol sulfate | 0.10 | 0.10 |
| Oleic acid | 0.01 | 0.01 |
| Ethanol | 30.00 | 15.00 |
| HFC-134a | 69.89 | 84.89 |

EXAMPLE IX

| Component | wt % |
|---|---|
| Albuterol | 0.1 |
| Vetrel 245 | 17.0 |
| Miglyol 840 | 9 |
| HFC-134a | 73.9 |

EXAMPLE X

| Component | wt % |
|---|---|
| Albuterol | 0.10 |
| Oleic acid | 0.01 |
| Ethanol | 10.00 |
| Vertrel 245 | 9.90 |
| HFC 134a | 79.99 |

EXAMPLE XI

| Component | wt % |
|---|---|
| Albuterol | 0.1 |
| Pluronic L-121 | 0.4 |
| Vertrel 245 | 16.6 |
| Miglyol 840 | 9 |
| HFC-134a | 73.9 |

EXAMPLE XII

| Component | wt % |
|---|---|
| Albuterol | 0.10 |
| Pluronic L-121 | 0.90 |
| Oleic acid | 0.01 |

-continued

| Component | wt % |
|---|---|
| Miglyol 840 | 9.00 |
| HFC 134a | 89.99 |

EXAMPLE XIII

| Component | wt % |
|---|---|
| Albuterol | 0.10 |
| Tetronic 150 R1 | 0.10 |
| Oleic Acid | 0.01 |
| Miglyol 840 | 9.80 |
| HFC-134a | 89.99 |

EXAMPLE XIV

| Component | A wt % | B wt % |
|---|---|---|
| Mometasone furoate | 0.10 | 0.10 |
| Oleic acid | 0.01 | 0.01 |
| Ethanol | 30.00 | 15.00 |
| HFC-134a | 69.89 | 84.89 |

EXAMPLE XV

| Component | wt % |
|---|---|
| Mometasone furoate | 0.1 |
| Oleic acid | 0.2 |
| Transcutol | 18.0 |
| HFC-134a | 81.7 |

EXAMPLE XVI

| Component | wt % |
|---|---|
| Mometasone furoate | 0.1 |
| Tween 20 | 0.1 |
| Miglyol 840 | 9.8 |
| HFC-134a | 90.0 |

EXAMPLE XVII

| Component | wt % |
|---|---|
| Mometasone furoate | 0.1 |
| Pluronic L-121 | 0.4 |
| Miglyol 840 | 9.0 |
| HFC-13a | 90.5 |

EXAMPLE XVIII

| Component | wt % |
|---|---|
| Mometasone furoate | 0.1 |
| Tetronic 150 R1 | 0.1 |
| Miglyol 840 | 9.8 |
| HFC-134a | 90 |

EXAMPLE XIX

| Component | wt % |
|---|---|
| Beclomethasone dipropionate | 0.1 |
| Oleic acid | 0.01 |
| Ethanol | 5 |
| HFC 134a | 94.89 |

EXAMPLE XX

| Component | wt % |
|---|---|
| Beclomethasone dipropionate P-11 clathrate | 0.1 |
| Oleic acid | .01 |
| Miglyol 840 | 1.5 |
| HFC-134a | 98.39 |

EXAMPLE XXI

| Component | wt % |
|---|---|
| Beclomethasone dipropionate hexane clathrate | 0.1 |
| Pluronic L121 | .01 |
| Miglyol 840 | 1.5 |
| HFC-134a | 98.3 |

EXAMPLE XXII

| Component | wt % |
|---|---|
| Mometasone Furoate | 0.1 |
| HFC-134a | 99.9 |

EXAMPLE XXIII

| Component | wt % |
|---|---|
| Beclomethasone Dipropionate P-11 Clathrate | 0.1 |
| HFC-134a | 99.9 |

EXAMPLE XXIV

| Component | wt % |
|---|---|
| Mometasone Furoate | 0.1 |
| Tween 20 | 0.01 |
| HFC-134a | 99.89 |

EXAMPLE XXV

| Component | wt % |
|---|---|
| Beclomethasone Dipropionate P-11 Clathrate | 0.1 |
| Tween 20 | 0.01 |
| HFC-134a | 99.89 |

EXAMPLE XXVI

| Component | wt % |
|---|---|
| Mometasone furoate | 0.1 |
| Tween 20 | 0.01 |
| Oleic Acid | 0.0005 |
| HFC-134a | 99.8895 |

EXAMPLE XXVII

| Component | wt % |
|---|---|
| Mometasone Furoate | 0.1 |
| Miglyol 840 | 9 |
| Oleic Acid | 0.005 |
| Tetronic 150 R1 | 0.01 |
| HFC-134a | 90.885 |

EXAMPLE XXVIII

| Component | wt % |
|---|---|
| Beclomethasone Dipropionate P-11 Clathrate | 0.1 |
| Miglyol 840 | 3 |
| Oleic Acid | 0.005 |
| Pluronic L 121 | 0.01 |
| HFC-134a | 96.885 |

EXAMPLE XXIX

| Component | wt % |
|---|---|
| Beclomethasone dipropionate | 0.1 |
| Oleic acid | 0.2 |
| Transcutol | 5 |
| HFC-134a | 94.7 |

EXAMPLE XXX

| Component | wt % |
|---|---|
| Beclomethasone dipropionate P-11 Clathrate | 0.1 |
| Pluronic L-121 | 0.1 |
| Miglyol 840 | 1.5 |
| HFC-134a | 98.7 |

EXAMPLE XXXI

| Component | wt % |
|---|---|
| Beclomethasone dipropionate | 0.1 |
| PEG 400 | 5 |
| HFC-134a | 94.9 |

EXAMPLE XXXII

| Component | wt % |
|---|---|
| Beclomethasone Dipropionate P-11 Clathrate | 0.1 |
| Miglyol 840 | 1.5 |
| HFC-134a | 94.9 |

While the examples above have been directed at albuterol, albuterol sulfate, mometasone furoate, beclomethasone dipropionate and beclomethasone dipropionate clathrates, it is contemplated that other orally or nasally administered medicaments could be utilized. Similarly, it is contemplated that excipients and surfactants other than those exemplified may be utilized.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An aerosol formulation comprising:
   A. an effective amount of mometasone furoate;
   B. 1,1,1,2-tetrafluoroethane; and
   C. optionally, one or more components selected from at least one of the following:
      excipients;
      surfactants; and
      additives which are;
         preservatives;
         buffers;
         antioxidants;
         sweeteners; and
         taste masking agents.

2. The formulation of claim 1 containing 0.01 to 1 percent by weight medicament.

3. The formulation of claim 1 containing 0.03 to 0.7 percent by weight medicament.

4. The formulation of claim 1 containing 0.05 to 0.5 percent by weight medicament.

5. The formulation of claim 1 wherein the medicament is a powder having a mean particle size of 1 to 5 microns.

6. The formulation of claim 1 which is substantially free of chlorofluorocarbons.

7. The formulation of claim 1 containing the following:

| Component | Weight Percent |
|---|---|
| Mometasone furoate | 0.01–1 |
| 1,1,1,2-Tetrafluoroethane | 25–99.99 |
| Excipient | 0–75 |
| Surfactant | 0–3 |

8. The formulation of claim 1 containing the following:

| Component | Weight Percent |
|---|---|
| Mometasone furoate | 0.03–0.7 |
| 1,1,1,2-Tetrafluoroethane | 50–99.97 |
| Excipient | 0–50 |
| Surfactant | 0–2 |

9. The formulation of claim 1 containing the following:

| Component | Weight Percent |
|---|---|
| Mometasone furoate | 0.05–0.5 |
| 1,1,1,2-Tetrafluoroethane | 50–99.95 |
| Excipient | 0–50 |
| Surfactant | 0–1 |

* * * * *